(12) United States Patent
Dejeaifve et al.

(10) Patent No.: US 10,414,697 B2
(45) Date of Patent: Sep. 17, 2019

(54) TOCOPHEROL STABILISERS FOR NITROCELLULOSE-BASED PROPELLANTS

(71) Applicant: PB CLERMONT SA, Engis (BE)

(72) Inventors: Alain Dejeaifve, Engis (BE); Rowan Dobson, Engis (BE)

(73) Assignee: PB CLERMONT, Engis (BE)

( * ) Notice: Subject to any disclaimer, the term of this patent is extended or adjusted under 35 U.S.C. 154(b) by 235 days.

(21) Appl. No.: 15/553,276

(22) PCT Filed: Feb. 25, 2016

(86) PCT No.: PCT/EP2016/053948
§ 371 (c)(1),
(2) Date: Aug. 24, 2017

(87) PCT Pub. No.: WO2016/135228
PCT Pub. Date: Sep. 1, 2016

(65) Prior Publication Data
US 2018/0029952 A1 Feb. 1, 2018

(30) Foreign Application Priority Data

Feb. 25, 2015 (EP) ..................... 15156490

(51) Int. Cl.
*C06B 25/26* (2006.01)
*C06B 23/00* (2006.01)
(Continued)

(52) U.S. Cl.
CPC ............ *C06B 23/006* (2013.01); *C06B 25/20* (2013.01); *C07D 311/72* (2013.01)

(58) Field of Classification Search
USPC ........................................ 149/88, 96, 97, 98
See application file for complete search history.

(56) References Cited

U.S. PATENT DOCUMENTS 2,249,054 A 7/1941 Smith et al.
2,846,435 A 8/1958 Harris
(Continued)

FOREIGN PATENT DOCUMENTS

EP 0 072 349 A2 2/1983
EP 0 273 868 A2 7/1988
(Continued)

OTHER PUBLICATIONS

European Search Report for corresponding Application No. 15156490.3 dated Jan. 8, 2016.
(Continued)

*Primary Examiner* — James E McDonough
(74) *Attorney, Agent, or Firm* — Norris McLaughlin, P.A.

(57) ABSTRACT

The present disclosure is directed to a nitrocellulose-based propellant composition comprising: (a) a nitrate ester based propellant comprising nitrocellulose; and (b) a stabilizer consisting of a tocopherol compound with a general formula (I),

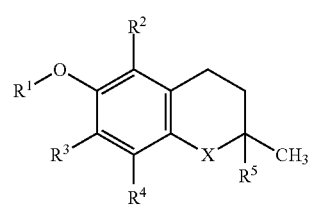

wherein: X is oxygen; $R^1$ is selected from the group consisting of hydrogen, alkyl, alkenyl, alkynyl, aryl, heteroaryl, carboxylic acid, carboxylate, ester, saccharide, alkoxy-linked saccharide, alcohol, and ethers; $R^2$ is selected from (Continued)

the group consisting of hydrogen methyl, benzyl carboxylic acid, benzyl carboxylate, benzylester and saccharide; $R^3$ is selected from the group consisting of hydrogen, methyl, benzyl carboxylic acid, benzyl carboxylate, benzylester and saccharide; $R^4$ is selected from the group consisting of methyl, benzyl carboxylic acid, benzyl carboxylate, benzylester and saccharide; and $R^5$ is selected from the group consisting of alkyl and alkenyl.

20 Claims, 5 Drawing Sheets

(51) Int. Cl.
  *C06B 25/20* (2006.01)
  *C07D 311/72* (2006.01)
  *C06B 25/24* (2006.01)
  *C06B 25/18* (2006.01)
  *C06B 25/00* (2006.01)

(56) References Cited

U.S. PATENT DOCUMENTS

| | | |
|---|---|---|
| 3,833,400 A | 9/1974 | Matsukawa et al. |
| 4,692,258 A | 9/1987 | Rasberger et al. |
| 4,965,006 A | 10/1990 | Meier et al. |
| 2011/0014096 A1* | 1/2011 | Fukuoka ............ B01L 3/50273 422/503 |

FOREIGN PATENT DOCUMENTS

| | | |
|---|---|---|
| WO | 9703974 A2 | 2/1997 |
| WO | 2005/019178 A1 | 3/2005 |
| WO | 2012/066126 A1 | 5/2012 |
| WO | 2014/016336 A1 | 1/2014 |

OTHER PUBLICATIONS

Wilker, Stephan, et al., "Stability Analysis of Propellants Containing New Stabilizers—part IV: are phenols a possible alternative to aromatic amines?", Fraunhofer—Institut fuer Chemische Technologie, Apr. 26, 2007, Swisttal, Germany.

Chin, Anton, et al., "Investigation of the decomposition Mechanism and Thermal Stability of Nitrocellulose/Nitroglycerine Based Propellants by Electron Spin Resonance", Wiley InterScience, Propellants, Explosives, Pyrotechnics, Apr. 1, 2007, pp. 117-126, vol. 32, No. 2; Wiley-VCH Verlag GmbH & Co., KGaA, Weinheim, Germany.

Venter, Andre., et al., "A Desorption Electrospray Ionization Mass Spectrometry Study of Aging Products of Diphenylamine Stabilizer in Double-base Propellants", Propellants, Esplosives, Pyrotechnics, Dec. 1, 2006, pp. 472-476, vol. 31, No. 6, Wiley-VCH Verlag GmbH & Co., Weinheim, Germany.

Nato Standarization Agency, "Explosives, nitrocellulose-based propellants, stability test procedure and requirements using heat flow calorimetry", 24 pages, STANAG 4582, Ed. 1, North Atlantic Treaty Organisation, Brussels, Belgium.

International Search Report for corresponding PCT Application No. PCT/EP2016/053948 dated Apr. 4, 2016.

International Written Opinion of the International Searching Authority for corresponding PCT Application No. PCT/EP2016/053948 dated Apr. 4, 2016.

* cited by examiner

TOCOPHEROL STABILISERS FOR NITROCELLULOSE-BASED PROPELLANTS

This application is a 371 application of PCT/EP2016/053948 filed 25 Feb. 2016, which claims foreign priority benefit under 35 U.S.C. § 119 of European application 15156490.3 filed 25 Feb. 2015.

TECHNICAL FIELD

The present invention relates to stabilised nitrocellulose-based propellant compositions. In particular it concerns nitrocellulose-based propellant stabilised with a stabiliser producing little to no carcinogenic and mutagenic by-products.

BACKGROUND FOR THE INVENTION

Smokeless powders have been developed since the 19th century to replace traditional black powder, which generates substantial amounts of smoke when fired. The most widely used smokeless powders are nitrocellulose-based. Nitrocellulose is obtained by using nitric acid to convert cellulose into cellulose nitrate and water according to a general reaction:

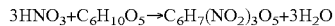

$$3HNO_3 + C_6H_{10}O_5 \rightarrow C_6H_7(NO_2)_3O_5 + 3H_2O$$

Nitrocellulose-based smokeless powder is then obtained by treating the thus obtained nitrocellulose by extrusion or spherical granulation, with or without solvent, two techniques which are well known to the persons skilled in the art.

Various improvements have been developed since the first discovery of nitrocellulose, by addition of further components, such as nitroglycerine and/or nitroguanidine allowing an increase of the detonation velocity. Pure nitrocellulose propellant is referred to as single-base propellant, and double- and triple-base propellants refer to compositions comprising nitrocellulose and one or two additional energetic bases, respectively, typically blasting oils such as nitroglycerine, nitroguanidine, or secondary explosives.

Nitrocellulose, as most nitrate esters, is prone to self-ignition as a result of thermal degradation due to the weakness of its O—N bond. When employed as an ingredient of propellants or other explosive compositions, the spontaneous ignition of nitrocellulose has caused serious accidents. It is obviously vital to inhibit or slow down this degradation for safety reasons but it is also important to retain the initial properties of the energetic composition. Degradation usually leads to gas emissions, heat generation and reduction of molecular mass affecting negatively the material structure and ballistic properties.

The decomposition of nitrocellulose usually starts with a bond scission or hydrolysis, generating alkoxy radicals and nitrogen oxide (NOx) species (cf. FIG. 1). The radicals further react generating more radicals, speeding up the degradation process, and ultimately lead to chain scission accompanied by heat generation. In order to prolong the service life of the propellants, stabilisers are added to the energetic mixture in order to scavenge these radical species and slow down the degradation pattern.

All conventional stabilisers used to date for nitrocellulose-based propellants belong to (a) aromatic amines (e.g., diphenylamine, 4-nitro-N-methylamine) or (b) aromatic urea derivatives (e.g., akardite, centralite) and are or produce toxic and/or potentially carcinogenic species at some point during the propellant's lifetime. For example, the most widely used stabilisers to date are diphenylamine, akardite, and centralite. These compounds, however, form carcinogenic derivatives such as N-nitrosodiphenylamine (cf. FIG. 2(a)) or N-nitrosoethylphenylamine.

Hindered amines, such as triphenylamine, reduce the formation of N—NO groups, but fail to stabilise nitrocellulose satisfactorily. Conventional hindered phenols used in the plastics industry have been tested and at short term stabilise nitrocellulose with little to no N—NO formation. The phenols are able to trap the alkoxy radicals generated during the degradation of nitrocellulose and thus form new, relatively stable alkoxy radicals, by delocalisation of an electron at the foot of electron-rich, hindered groups as illustrated in FIG. 2(b). Long term stability is, however, not always guaranteed, probably due to rapid phenol depletion and relative stability of the newly formed alkoxy radicals.

WO20105019178 describes nitrocellulose-based propellants stabilised by substituted tetrahydroquinolines.

WO2012066126, WO2014016336, U.S. Pat. No. 2,249,054, and WO9703974 describe polymers comprising tocopherols and/or tocotrienols as anti-oxidants and as stabilisers.

There thus remains in the field of solid propellants a need for stabilisers allowing long term stabilisation of nitrocellulose-based propellants, fulfilling at least STANAG 4582 (Ed. 1) and which do not produce carcinogenic and/or mutagenic by-products. The present invention proposes a family of stabilisers fulfilling both above requirements. These and other advantages of the present invention are presented in continuation.

SUMMARY OF THE INVENTION

The present invention is defined in the appended independent claims. Preferred embodiments are defined in the dependent claims. In particular, the present invention concerns a nitrocellulose-based propellant composition comprising:
(a) a nitrate ester-based propellant comprising nitrocellulose; and
(b) a stabiliser consisting of a tocopherol or a tocotrienol-type compound, with a general formula (I):

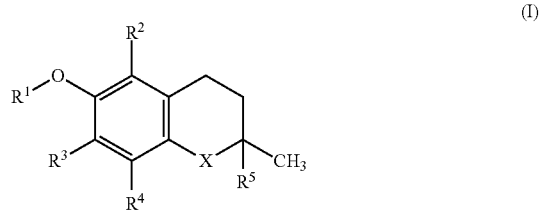

(I)

wherein:
X is oxygen;
$R^1$ is selected from the group consisting of hydrogen, alkyl, alkenyl, alkynyl, aryl, heteroaryl, carboxylic acid, carboxylate, ester, saccharide, alkoxy-linked saccharide, alcohol and ether;
$R^2$ is selected from the group consisting of hydrogen methyl, benzyl carboxylic acid, benzyl carboxylate, benzylester and saccharide;
$R^3$ is selected from the group consisting of hydrogen, methyl, benzyl carboxylic acid, benzyl carboxylate, benzylester and saccharide;
$R^4$ is selected from the group consisting of methyl, benzyl carboxylic acid, benzyl carboxylate, benzylester and saccharide;

$R^5$ is selected from the group consisting of alkyl and alkenyl.

The nitrate ester-based propellant may be a single base propellant consisting of nitrocellulose alone or, alternatively, may be a double or higher base propellant comprising nitrocellulose in combination with at least one blasting oil and/or at least one energetic additive. As known by a person skilled in the art, a blasting oil is herein defined as an energetic compound obtained by nitration of a polyol such as glycerol, glycol, diethylene glycol, triethylene glycol, metriol. The obtained nitrate is most of the time heavy, oily and presents explosive properties. Nitroglycerine is probably the most common blasting oil employed in the industry. The term "NOx" is used herein in its generally recognised sense, as a generic term for mono-nitrogen oxides NO and $NO_2$ (nitric oxide and nitrogen dioxide). In a preferred embodiment, the blasting oil comprises at least a nitrated polyol, said nitrated polyol is obtained by nitration of polyol selected from a group consisting of glycerol, glycol, diethylene glycol, triethylene glycol and metriol, preferably glycerol.

Energetic additives suitable for the present invention, like blasting oils, are used to enhance the blasting power of nitrocellulose. Energetic additives can be an energetic plasticiser or an explosive. Examples of energetic plasticisers comprise nitramines, such as butyl-NENA or dinitrodiazaalkane (DNDA). Examples of explosives suitable for use as energetic additives include RDX, HMX, FOX7, FOX12, CL20.

The preferred stabilisers of the present invention are capable of reacting with both degradation products of the nitrate ester: alkoxy radicals and NOx. Firstly, by hydrogen abstraction of the labile proton of the stabiliser, by reaction with the alkoxy radical groups, thus forming a stable alcohol compound and a first by-product able to trap the NOx species. The thus formed successive by-products are capable of reacting with NOx and alkoxy radicals from the degradation of the nitrate ester. No harmful NNO groups are formed due to the lack of nitrogen atoms in the stabiliser structure.

The preferred stabilisers of the present invention are capable of reacting with radical alkoxy groups formed by degradation of the nitrate ester by H-abstraction to form a first by-product capable of reacting with NOx formed by degradation of the nitrate ester to form a second by-product comprising no NNO groups. It is even more preferred if the second by-product is itself also capable of reacting with radical alkoxy groups or with NOx formed by degradation of the nitrate ester forming third by-products. Optimally, the third and subsequent by-products are also capable of reacting with such radical alkoxy groups or with NOx, thus substantially prolonging the efficacy of the stabiliser.

It is preferred that the blasting oil comprises at least a nitrated polyol, said nitrated polyol is obtained by nitration of polyol selected from a group consisting of glycerol, glycol, diethylene glycol, triethylene glycol and metriol, preferably glycerol.

In a preferred embodiment, the stabiliser is selected from a group consisting of alpha-tocopherol, beta-tocopherol, gamma-tocopherol, delta-tocopherol, alpha-tocotrienol, beta-tocotrienol, gamma-tocotrienol, delta-tocotrienol or a mixture thereof.

In a preferred embodiment, the stabiliser is selected from a group consisting of (+)-alpha-tocopherol, (+)-beta-tocopherol, (+)-gamma-tocopherol, (+)-delta-tocopherol, (−)-alpha-tocopherol, (−)-beta-tocopherol, (−)-gamma-tocopherol, (−)-delta-tocopherol or a mixture thereof.

A preferred stabiliser is (+)-alpha-tocopherol, of formula (Ia):

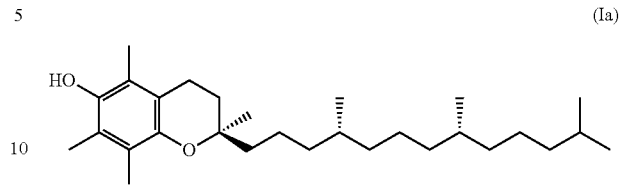

(Ia)

The stabiliser may be present in the composition in an amount comprised between 0.1 and 5.0 wt. %, preferably between 0.2 and 2.0 wt. %, more preferably between 0.5 and 1.5 wt. %, with respect to the total weight of the composition. The nitrate ester-based propellant may comprise nitrocellulose only, thus defining a single base propellant or, alternatively, it may comprise a blasting oil, such as nitroglycerine, to define a double base propellant. A double base propellant according to the present invention preferably comprises not more than 60 wt. % nitroglycerine, and preferably comprises between 5 and 45 wt. %, more preferably between 7 and 22 wt. % nitroglycerine, with respect to the total weight of nitrate ester-based propellant.

The propellant compositions of the present invention should fulfil the stability requirements defined in STANAG 4582 (Ed. 1), namely generating less than 350 μW/g of heat flow for at least 3.43 days at a temperature of 90° C. Many propellant compositions of the present invention can achieve much better that this and may remain stable for over 30 days at 90° C.

In a preferred embodiment, the stabiliser is used in combination with a complementary stabiliser. The complementary stabiliser is preferably selected from the following group:
  (a) a substituted phenol compound (13) having the general formula (13-I):

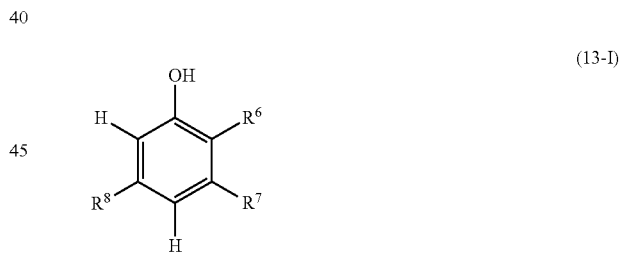

(13-I)

wherein: $R^6$ represents: (i) H, (ii) alkyl substituted or not, or (iii) an alkoxy group; and $R^7$- and $R^8$ are same or different, and represent (i) alkyl substituted or not, or (ii) alkoxy group;
  (b) a trialkoxy benzene (14) having the general formulae (14-I) or (14-II):

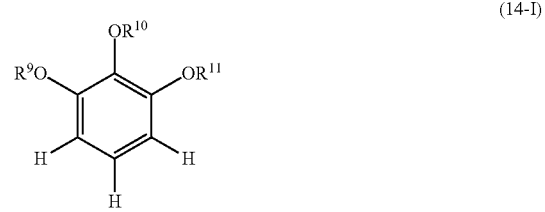

(14-I)

-continued

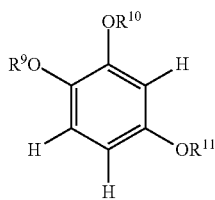
(14-II)

wherein $R^9$, $R^{10}$ and $R^{11}$ are same or different and represent $C_{1-5}$ alkyl unsubstituted or substituted with an alkoxy group; and (c) an aromatic compound (15) having a general formula (15-I):

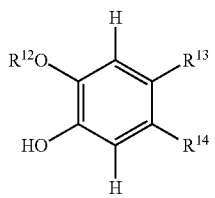
(15-I)

Wherein: $R^{12}$ represents, alkyl substituted or not; $R^{13}$ represent (i) H, (ii) unsaturated alkyl group,
(iii)

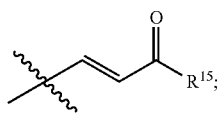

(iv)

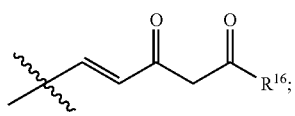

or
(v)

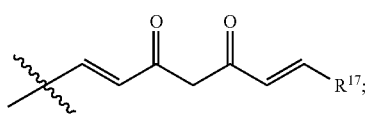

$R^{14}$ represents, H, alkyl substituted or not, or $OR^{18}$;
$R^{15}$ represents, alkyl substituted or not, aromatic ring substituted or not, or $OR^{18}$;
$R^{16}$ represents, alkyl substituted or not, aromatic ring substituted or not, or $OR^{19}$;
$R^{17}$ represents, aromatic ring substituted or not;
$R^{18}$ represents, alkyl substituted or not, or aromatic ring substituted;
$R^{19}$ represents, alkyl substituted or not, or aromatic ring substituted.

(d) a substituted phenol compound (16) having the general formula (16-I):

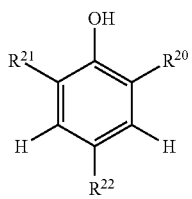
(16-I)

wherein: $R^{20}$, $R^{21}$ and $R^{22}$ are the same or different and represent: (i) alkyl-substituted or not, (ii) alkoxy group.

(e) a substituted phenol compound (17) having the general formula (17-I):

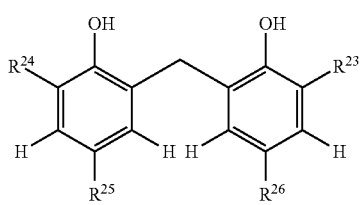
(17-I)

wherein: $R^{23}$, $R^{24}$, $R^{25}$ and $R^{26}$ are the same or different and represent: (i) alkyl-substituted or not, (ii) alkoxy group.

(f) a compound of the ionone-type, with a general formula (18-I), (18-II), (18-III) or (18-IV):

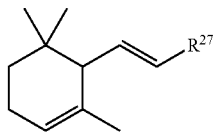
(18-I)

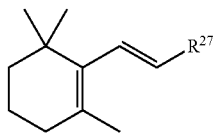
(18-II)

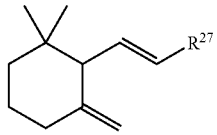
(18-III)

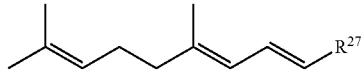
(18-IV)

wherein $R^{27}$ represents a ketone, hydroxyl, carboxyl, aldehyde or unsaturated alkyl group Beside a nitrate ester-based propellant and a stabiliser, the propellant compositions of the present invention may comprise additives. In particular, they may comprise one or more of the following additives:

(a) a potassium salt, such as potassium nitrate ($KNO_3$) or sulphate ($K_2SO_4$), preferably in an amount comprised between 0.01 and 1.5 wt. %;

(b) combustion moderators such as phthalates, Cl and citrate derivatives, preferably in an amount comprised between 1.0 and 10.0 wt. %;

(c) an anti-static agent such as graphite, preferably in an amount comprised between 0.01 and 0.5 wt. %; and (d) calcium carbonate, preferably in an amount comprised between 0.01 and 0.7 wt. %, Wherein the wt. % are expressed in terms of the total weight of the propellant composition.

The present invention also concerns the use of a stabiliser of formula (I) as defined above, for stabilising a nitrocellulose based propellant composition. The stabiliser is preferably of a formula (Ia) as defined supra.

BRIEF DESCRIPTION OF THE FIGURES

For a fuller understanding of the nature of the present invention, reference is made to the following detailed description taken in conjunction with the accompanying drawings in which.

DETAILED DESCRIPTION OF THE INVENTION

Figure 1:
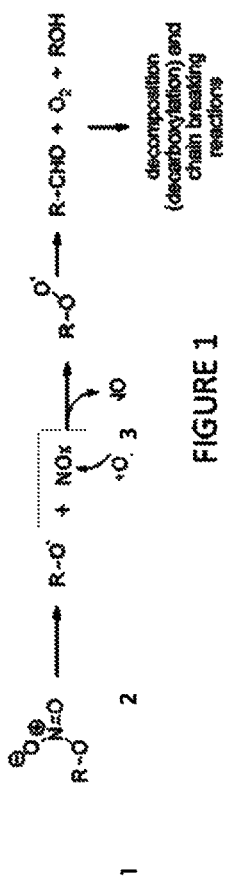
FIG. 1: shows a reaction of spontaneous decomposition of nitrocellulose with formation of free radicals and NOx.
Figure 2A:
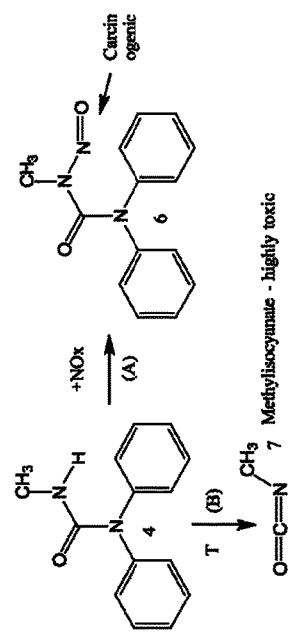
FIG. 2: shows the assumed stabilisation mechanisms of akardite (AkII) and diphenylamine (DPA) (prior art).
Figure 2B:
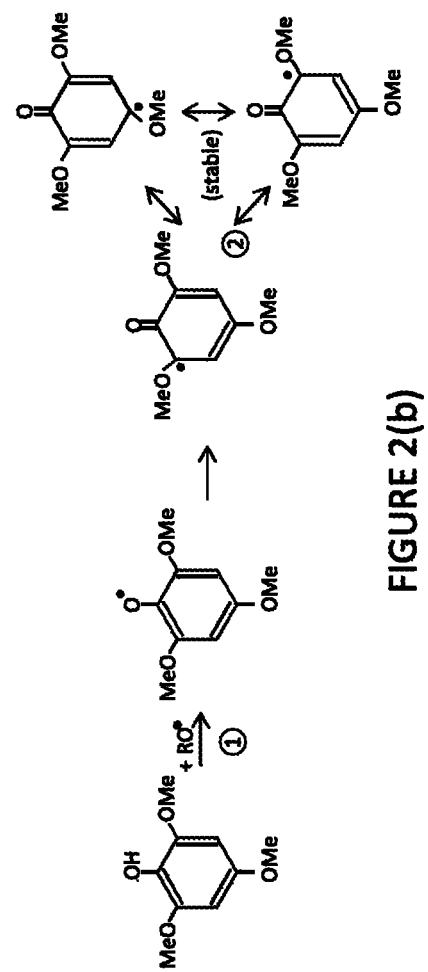

As illustrated in FIG. 1, degradation of nitrocellulose forms free oxide radicals 2 (R—O) and NOx. These degradation products are capable of reacting further and with nitrocellulose 1, which can rapidly lead to an explosion of the nitrate ester-based propellant due to excess heat generation. The most commonly used stabilisers are certainly akardite (AkII) 4 and diphenyl amine (DPA) 5 as illustrated in FIG. 2(a). Akardite (AkII) 4 when exposed to NOx, forms carcinogenic N—NO compounds 6 as illustrated in reaction (A) of FIG. 2(a). Simultaneously or sequentially, it dissociates upon exposure to heat to form diphenyl amine (DPA) 5 following reaction (B) of FIG. 2(a). Whether used directly as stabiliser, or present in the composition following heat dissociation (B) of akardite 4, diphenyl amine (DPA) 5 stabilises a propellant composition by the following mechanism. A free radical alkoxy group generated by the propellant abstracts the hydrogen of the amine group of DPA 5 to form a stable compound (ROH, 9) (cf. reaction of FIG. 2(a)). The radical formed on the amine 8 can react with a NOx to form stable N-nitrosodiphenylamine 10 (cf. reaction (D) of FIG. 2(a)). The NNO group of N-nitrosodiphenylamine 10 is, however, carcinogenic and should be avoided for safety reasons. Triphenylamine has been tested in the past in order to prevent formation of NNO groups, but with little success in stabilisation properties. Hindered phenols as illustrated in FIG. 2(b) effectively react with free oxide radicals (R—O') but forming stable components which are unlikely to further react with NOx (cf. reaction 1̂ of FIG. 2(b)). The efficiency of such stabilisers is limited to short periods of time only because of rapid phenol depletion.

A stabiliser as used in the present invention has a general formula (I)

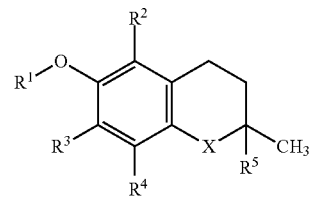

wherein:
X is oxygen;
$R^1$ is selected from the following: hydrogen, alkyl, alkenyl, alkynyl, aryl, heteroaryl, carboxylic acid, carboxylate, ester, saccharide, alkoxy-linked saccharide, alcohol and ether groups;
$R^2$ is selected from the group consisting of hydrogen methyl, benzyl carboxylic acid, benzyl carboxylate, benzylester and saccharide;
$R^3$ is selected from the group consisting of hydrogen, methyl, benzyl carboxylic acid, benzyl carboxylate, benzylester, and saccharide;
$R^4$ is selected from the group consisting of methyl, benzyl carboxylic acid, benzyl carboxylate, benzylester, and saccharide;
$R^5$ is selected from the group consisting of alkyl and alkenyl.

Not wishing to be bound by any theory, it is believed that a stabiliser (I), as defined in the present invention contains a very labile proton which can react with radical alkoxy groups 2 and NOx species (FIG. 1) formed by degradation of the nitrate ester 1. Successive by-products are likely formed, and are also capable of reacting with NOx and alkoxy radicals from the degradation of the nitrate ester 1, increasing the efficiency of stabiliser function. Since no harmful NNO groups are formed due to the lack of nitrogen atoms in compound (I) structure, the stabiliser according to the present invention produces little to no carcinogenic and mutagenic by-products.

In a preferred embodiment, the stabiliser is selected from a group consisting of alpha-tocopherol, beta-tocopherol, gamma-tocopherol, delta-tocopherol, alpha-tocotrienol, beta-tocotrienol, gamma-tocotrienol, delta-tocotrienol or a mixture thereof.

In a preferred embodiment, the stabiliser is selected from a group consisting (+)-alpha-tocopherol, (+)-beta-tocopherol, (+)-gamma-tocopherol, (+)-delta-tocopherol, (−)-alpha-tocopherol, (−)-beta-tocopherol, (−)-gamma-tocopherol, (−)-delta-tocopherol or a mixture thereof.

A preferred stabiliser is (+)-alpha-tocopherol, of formula (Ia):

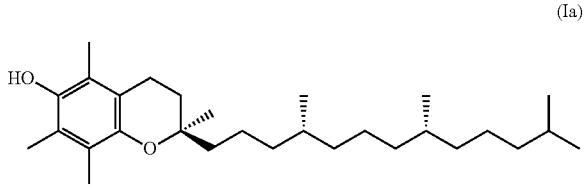 [SMILES: Cc1c(C)c2c(c(C)c1O)CC[C@@](C)(CCC[C@H](C)CCC[C@H](C)CCCC(C)C)O2]

Figure 3A:
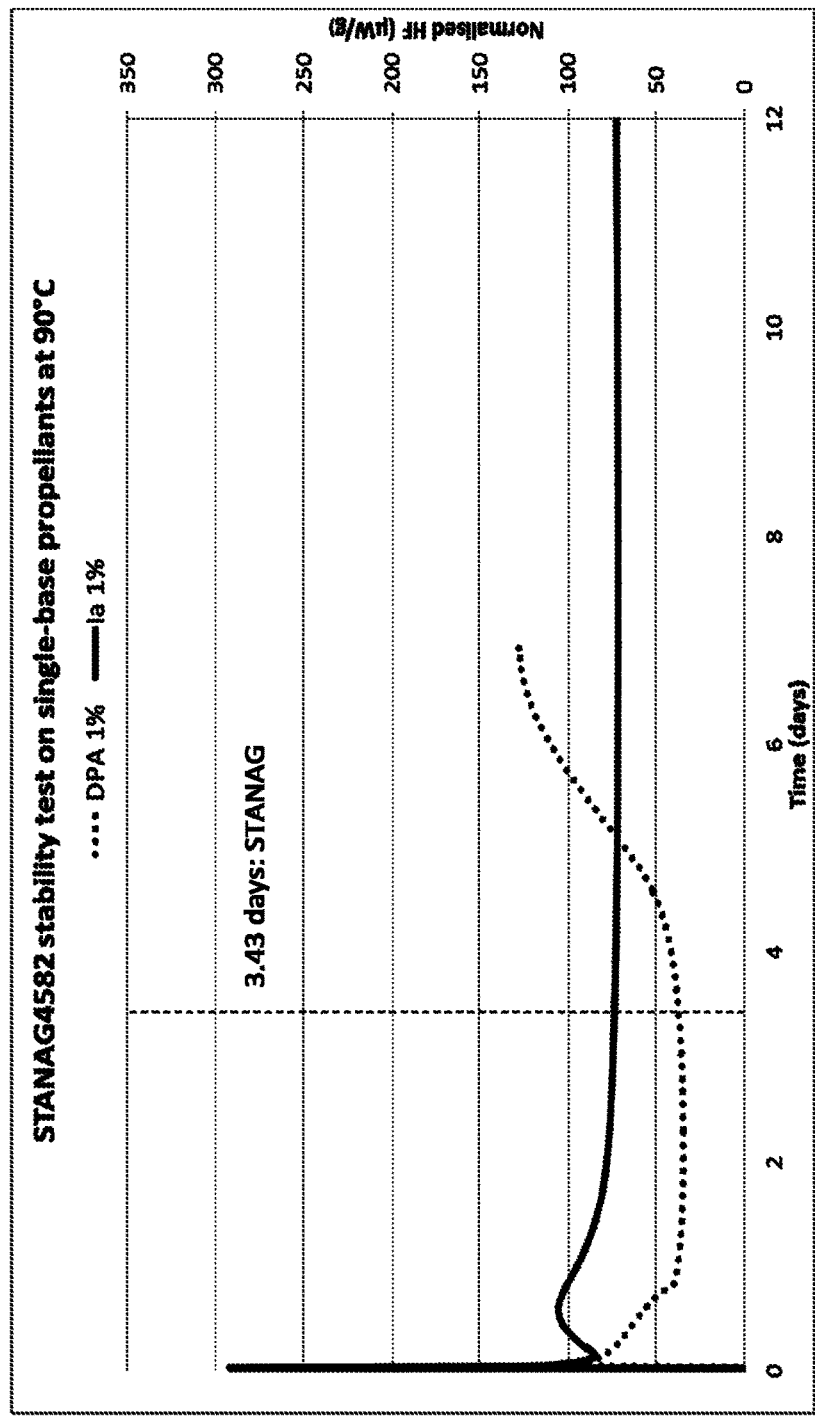
FIG. 3: shows the normalised heat flow expressed in μW/g generated by propellant compositions stabilised with various amounts of a stabiliser of formula (Ia) for (a) single base nitrocellulose propellants, (b) double base nitrocellulose/nitroglycerine (80/20 wt. %) propellants and (c) double base nitrocellulose/nitroglycerine (60/40 wt. %) propellants.
Figure 3B:
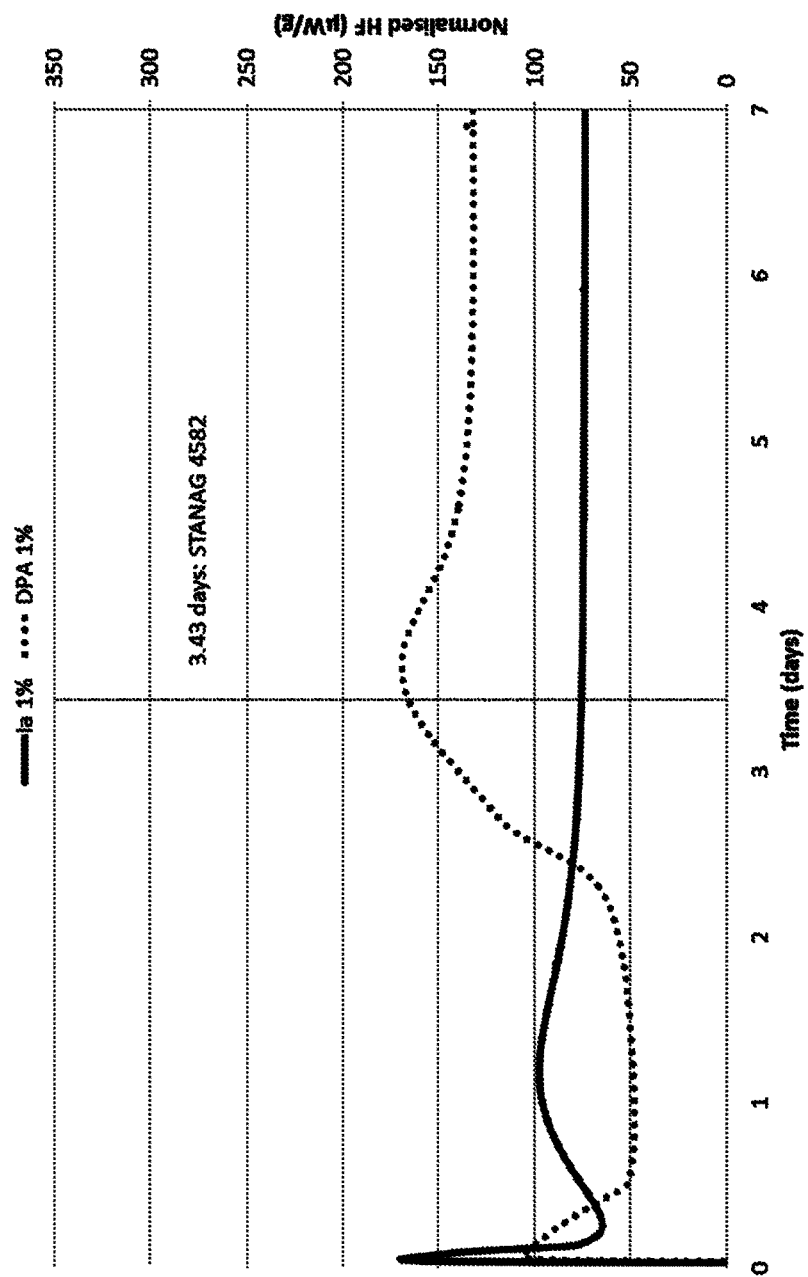
Figure 3C:
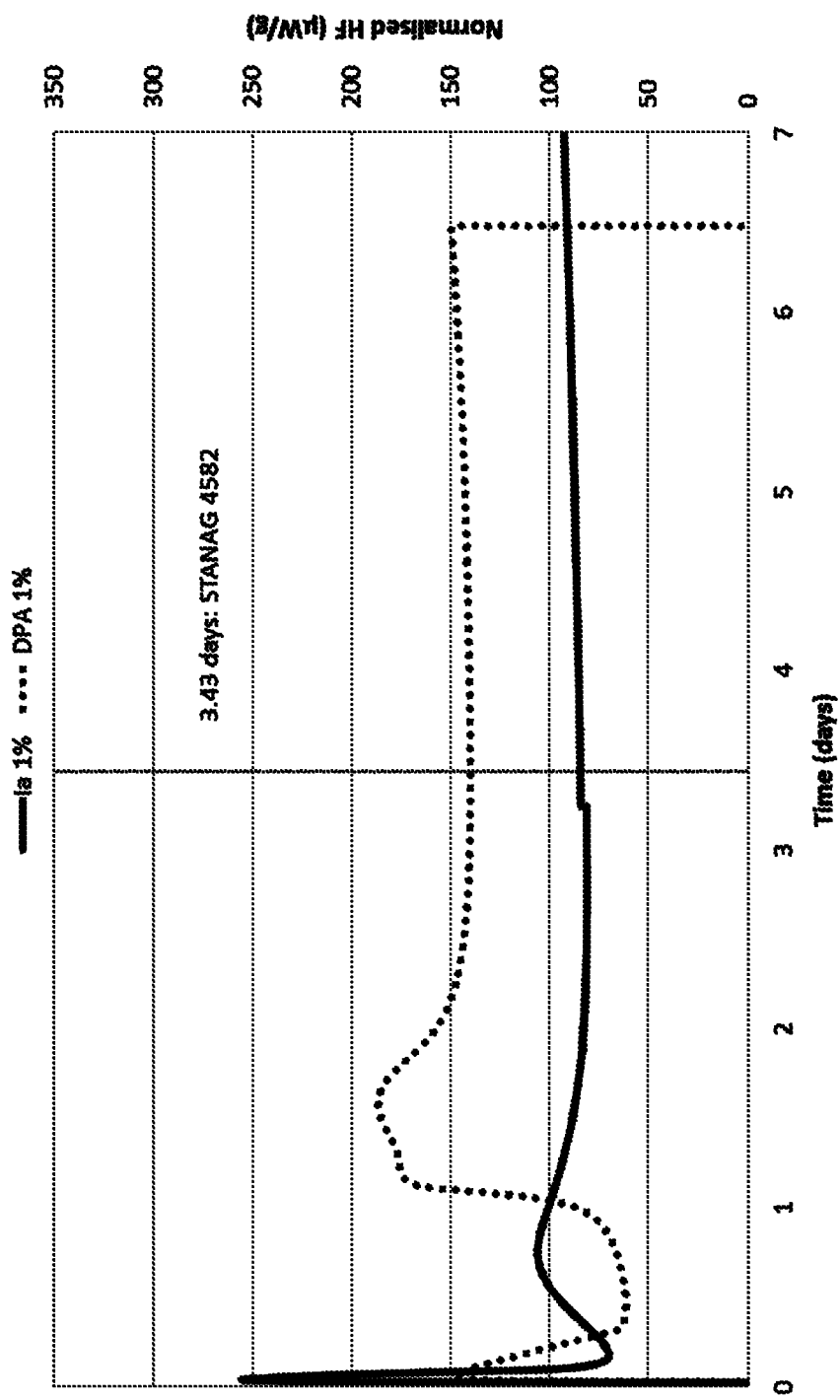

The propellant composition may be a single base propellant, wherein the nitrate ester propellant consists of nitrocellulose only or a double base propellant, wherein nitrocellulose is combined with a blasting oil and/or at least one energetic additive. The most common blasting oil is nitroglycerine. FIG. 3(a) illustrates the stability of a single base propellant composition stabilised with a stabiliser (Ia) according to the present invention. FIG. 3(b) illustrates the same for a double base propellant composition wherein the nitrate ester propellant comprises 80 wt. % nitrocellulose and 20 wt. % nitroglycerine, a commonly used blasting oil. FIG. 3(c) illustrates the same for a double base propellant composition wherein the nitrate ester propellant comprises 60 wt. % nitrocellulose and 40 wt. % nitroglycerine. Energetic additives can be an energetic plasticiser selected from the group of nitramines such as butyl-NENA, dinitrodiazaalkane (DNDA), or an explosive such as RDX, HMX, FOX7, FOX12, CL20. A double base propellant composition according to the present invention preferably comprises a nitrate ester based propellant comprising not more than 60 wt. % blasting oil (such as nitroglycerine) or energetic additive with respect to the total weight of nitrate ester based propellant. More preferably, it comprises between 5 and 45 wt. %, most preferably between 7 and 22 wt. % blasting oil or energy additive, with respect of the total weight of nitrate ester based propellant. A preferred blasting oil is nitroglycerine.

A propellant composition according to the present invention comprises a stabiliser of formula (I), preferably in an amount comprised between 0.1 and 5.0 wt. %, more preferably between 0.2 and 2.0 wt. %, most preferably between 0.5 and 1.5 wt. %, with respect to the total weight of the composition. FIG. 3(a) compares the stability as a function of time of a single base propellant composition stabilised with DPA (dotted line, =prior art), and with 1 wt. % of a stabiliser according to formula (Ia) (solid line, =invention). FIGS. 3(b) & (c) plot the same stability curves as a function of time for double base propellant compositions (20 and 40% nitroglycerine, respectively) stabilised with DPA (dotted line) and with 1 wt. % of a stabiliser according to formula (Ia). It can be seen in FIG. 3 that a stabiliser of Formula (1a) maintains the level of energy released perfectly stable below 100 μW/g for over a week and longer. The stabilising properties of a stabiliser according to the present invention are at least as good—and often substantially better—than the ones of DPA, without forming any carcinogenic NNO-components.

Even longer stabilisation times can be obtained by combining a stabiliser as defined in the present invention with a complementary stabiliser in the form of an aromatic compound. The complementary stabiliser is preferably selected from the following group:

(a) a substituted phenol compound (13) having the general formula (13-I):

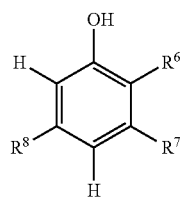

(13-I)

wherein: $R^6$ represents: (i) H, (ii) alkyl substituted or not, or (iii) an alkoxy group; and $R^7$ and $R^8$ are same or different, and represent (i) alkyl substituted or not, or (ii) alkoxy group;

(b) a trialkoxy benzene (14) having the general formulae (14-I) or (14-II):

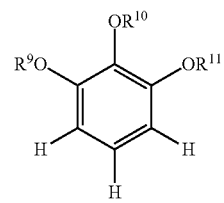

(14-I)

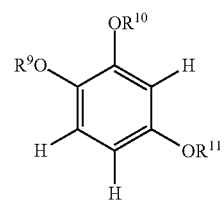

(14-II)

wherein $R^9$, $R^{10}$ and $R^{11}$ are same or different and represent $C_{1-5}$ alkyl unsubstituted or substituted with an alkoxy group; and (c) an aromatic compound (15) having a general formula (15-I):

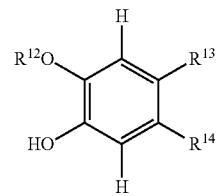

(15-I)

Wherein: $R^{12}$ represents, alkyl substituted or not; $R^{13}$ represent (i) H, (ii) unsaturated alkyl group, (iii)

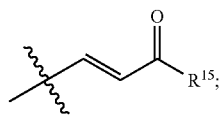

(iv)

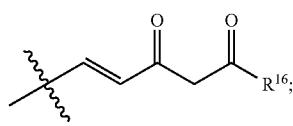

or (v)

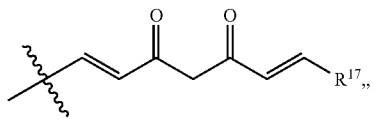

$R^{14}$ represents, H, alkyl substituted or not, or $OR^{18}$;

$R^{15}$ represents, alkyl substituted or not, aromatic ring substituted or not, or $OR^{18}$;

$R^{16}$ represents, alkyl substituted or not, aromatic ring substituted or not, or $OR^{19}$;

$R^{17}$ represents, aromatic ring substituted or not;

$R^{18}$ represents, alkyl substituted or not, or aromatic ring substituted;

$R^{19}$ represents, alkyl substituted or not, or aromatic ring substituted.

In a preferred embodiment, $R^{12}$ represents $C_{1-5}$ alkyl-substituted or not, preferably $CH_3$; further, it is preferred that $R^{13}$ represents:

(i)

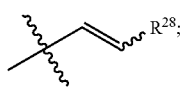

(ii)

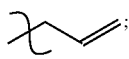

(iii)

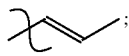

or (iv)

Wherein R28 represents H, alkyl-substituted or not, or aromatic ring, substituted or not. For example, eugenol (15-III) or isoeugenol (15-IV) are suitable complementary stabilisers according to the present invention.

(15-III)

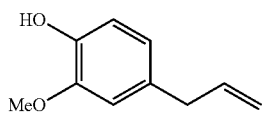

(15-IV)

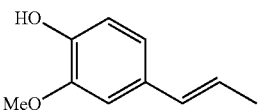

A more preferred embodiment of composition according to the present invention comprises a curcumin derivative of formula (15-II) as stabiliser, (15-II)

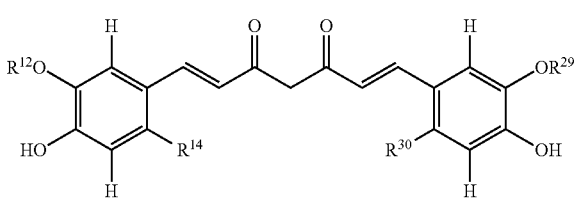

Wherein $R^{12}$ and $R^{29}$ are same or different and represent alkyl substituted or not, preferably $C_{1-5}$, more preferably $CH_3$; $R^{14}$ and $R^{30}$ are same or different and represent H or alkyl substituted or not (e.g., $C_{1-5}$ alkyl), wherein each of $R^{12}$ and $R^{29}$, and $R^{14}$ and $R^{30}$, are preferably same, and more preferably both are H.

(d) a substituted phenol compound (16) having the general formula (16-I):

(16-I)

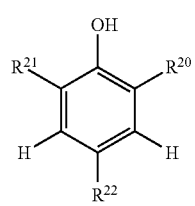

wherein: $R^{20}$, $R^{21}$ and $R^{22}$ are the same or different and represent: (i) alkyl-substituted or not, (ii) alkoxy group.

(e) a substituted phenol compound (17) having the general formula (17-I):

(17-I)

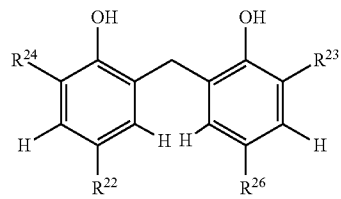

wherein: $R^{23}$, $R^{24}$, $R^{25}$ and $R^{26}$ are the same or different and represent: (i) alkyl-substituted or not, (ii) alkoxy group.

(f) a compound of the ionone-type, with a general formula (18-I), (18-II), (18-III) or (18-IV):

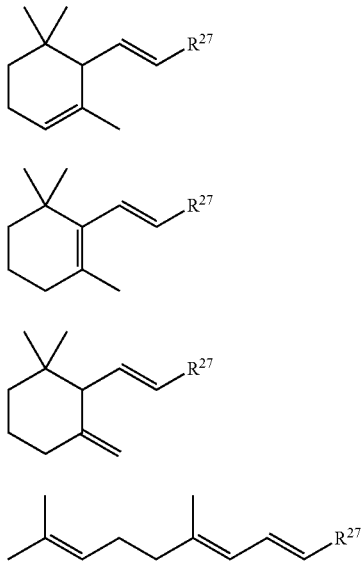

wherein $R^{27}$ represents a ketone, hydroxyl, carboxyl, aldehyde or unsaturated alkyl group. In a preferred embodiment, $R^{27}$ represents —C(O)CH$_3$ giving rise to alpha ionone (18-Ia) and pseudo ionone (18-IVb):

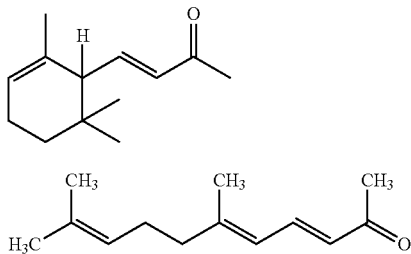

Beside a nitrate ester based propellant and a stabiliser, a propellant composition according to the present invention may comprise additives. In particular, it may comprise one or more of the following additives:

(a) a potassium salt, such as potassium nitrate (KNO$_3$) or sulphate (K$_2$SO$_4$), preferably in an amount comprised between 0.01 and 1.5 wt. %;

(b) combustion moderators such as phthalates, centralite and citrate derivatives, preferably in an amount comprised between 1.0 and 10.0 wt. %;

(c) an anti-static agent such as graphite, preferably in an amount comprised between 0.01 and 0.5 wt. %; and (d) calcium carbonate, preferably in an amount comprised between 0.01 and 0.7 wt. %, Wherein the wt. % are expressed in terms of the total weight of the propellant composition.

An example of propellant composition according to the present invention is listed in Table 1.

TABLE 1 typical propellant compositions according to the present invention

| component | single base wt. % | double base wt. % |
|---|---|---|
| nitrocellulose | 89.0-96.0 | 82.0-86.0 |
| nitroglycerine | 0.0 | 7.0-11.0 |
| KNO$_3$ | 0.5-1.0 | 0.5-1.0 |
| dibuthylphthalate | 3.0-7.0 | 3.0-7.0 |
| graphite | 0.2-0.4 | 0.2-0.4 |
| calcium carbonate | <0.7 | <0.7 |
| stabiliser of formula (I) | 0.15-2.0 | 0.15-2.0 |

Experimental Tests

STANAG 4582 (Ed. 1) of Mar. 9, 2007 entitled "*Explosives, nitrocellulose based propellants, stability test procedure and requirements using heat flow calorimetry*", defines an accelerated stability test procedure for single-, double-, and triple base propellants using heat flow calorimetry (HFC). The test is based on the measurement of the heat generated by a propellant composition at a high temperature. Fulfilment of the STANAG 4582 (Ed. 1) test qualifies a propellant composition for a 10 year stability at 25° C.

A sample of propellant composition is enclosed in a hermetically sealed vial and positioned in a heat flow calorimeter having a measuring range corresponding to 10 to 500 µW/g. The sample is heated and maintained at a constant temperature of 90° C. for the whole duration of the test and the heat flow is measured and recorded. A heat flow not exceeding 350 µW/g for a period of 3.43 days at 90° C. is considered to be equivalent to at least 10 years of safe storage at 25° C. The graphs of FIGS. 3(*a*), (*b*), and (*c*) show the stability of a composition as a function of time measured as defined above. The full scale of the ordinate (normalised heat flow) corresponds to a value of 350 µW/g not to be exceeded according to STANAG 4582 (Ed. 1), and the vertical straight line indicates 3.43 days. The initial heat flow peaks of graphs of FIGS. 3*a*, *b* and *c* are ignored as they are not representative of any specific reaction or phase transformation of the propellant composition, provided they do not exceed an exotherm of 5 J.

FIGS. 3(*a*), (*b*) and (*c*) show the results as solid lines of the stability tests carried out on single- and double-base nitrocellulose based propellants, the double base propellants comprising 20 wt. % (FIG. 3(*b*)) or 40 wt. % nitroglycerine (FIG. 3(*c*)), in all cases stabilised with 1 wt. % of a stabiliser according to formula (Ia), with respect to the total weight of the propellant composition. For comparison, the result of the same stability tests carried out on similar nitrocellulose based propellants, but stabilised with diphenyl amine (DPA) are plotted as dotted lines in the graphs of FIG. 3. It can be seen that the heat flow never exceeds 100 µW/g for 3.43 days, when STANAG 4582 (Ed. 1) requires to maintain the heat flow below 350 µW/g (full scale of the ordinate). The tests on single base propellants were carried out for a longer period, showing a prolonged stability of the compositions with a heat flow continuously lower than 150 µW/g for over 12 days.

Both DPA and stabiliser (1a) fulfill the requirements of STANAG 4582 (Ed. 1). Stabiliser (Ia) according to the present invention is, however, advantageous over DPA and Akardite because, (a) Contrary to DPA, stabilisers according to the present invention do not generate any N—NO carcinogenic by-product upon their stabilisation activity.

(b) DPA curve (dashed line) shows a sharp peak stabilising in a plateau at higher heat flow values, suggesting that all DPA was spent after only about two days (cf. reactions (C) & (D) in FIG. 2(a)) whence stabilisation probably proceeds by reactions with by-products. By contrast, no discontinuity in the heat flow can be identified with stabiliser (Ia) over 3.5 days. and even for over 12 days, as revealed in FIG. 3(a) discussed supra with respect to single base nitrocellulose propellants.

(c) As revealed in FIG. 3(a) discussed supra with respect to single base nitrocellulose propellants, the stabilisers of the present invention allow the maintenance of a heat flow substantially lower than 350 µW/g at a temperature of 90° C. for periods well over 12 days for single-base propellants. Double-base propellants with 20 wt. % and 40 wt. % nitroglycerine are perfectly stabilised for at least 7 or even 10 days. Longer term tests with DPA, however, are not easily performed because vials containing a composition stabilised with DPA leaked earlier than the ones stabilised according to the present invention. It is assumed that gas generation by the reactions with DPA raises the pressure inside the vials above their limit of resistance, leading to the bursting open of the vials after a few days testing. Uncontrolled pressure rises must be avoided during transportation or storage of propellant compositions for obvious reasons.

The propellant compositions of the present invention mark the beginning of the use of a new generation of stabilisers which can be referred to as "green or environmentally-friendly stabilisers," which combine efficient, long term stability of nitrocellulose-based propellants without formation of any detectable amounts of carcinogenic or mutagenic by-products.

The invention claimed is:

1. A nitrocellulose-based propellant composition comprising:
    (a) a nitrate ester based propellant comprising nitrocellulose; and
    (b) a stabiliser consisting of a tocopherol compound with a general formula (I),

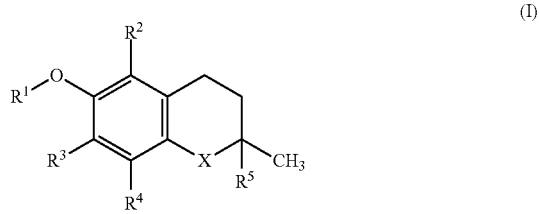

wherein:
X is oxygen;
$R^1$ is selected from the group consisting of hydrogen, alkyl, alkenyl, alkynyl, aryl, heteroaryl, carboxylic acid, carboxylate, ester, saccharide, alkoxy-linked saccharide, alcohol, and ethers;
$R^2$ is selected from the group consisting of hydrogen methyl, benzyl carboxylic acid, benzyl carboxylate, benzylester and saccharide;
$R^3$ is selected from the group consisting of hydrogen, methyl, benzyl carboxylic acid, benzyl carboxylate, benzylester and saccharide;
$R^4$ is selected from the group consisting of methyl, benzyl carboxylic acid, benzyl carboxylate, benzylester and saccharide; and
$R^5$ is selected from the group consisting of alkyl and alkenyl.

2. The propellant composition according to claim 1, wherein the nitrate ester based propellant consists of nitrocellulose alone as a single base or of a mixture comprising nitrocellulose in combination with at least a blasting oil and/or at least one energetic additive as a double or higher base.

3. The propellant composition according to claim 1, wherein the stabiliser is a component capable of reacting by H-abstraction with radical alkoxy groups formed by degradation of the nitrate ester to form a first by-product capable of reacting with NOx formed by degradation of the nitrate ester to form a second by-product comprising no NNO groups.

4. The propellant composition according to claim 3, wherein the second by-product is capable of reaction with radical alkoxy groups or with NOx formed by degradation of the nitrate ester to form a third and subsequent by-products capable of reacting with such radical alkoxy groups or with NOx.

5. The propellant composition according to claim 2, wherein the blasting oil comprises at least a nitrated polyol obtainable by nitration of a polyol selected from a group consisting of glycerol, glycol, diethylene glycol, triethylene glycol and metriol, and wherein the at least one energetic additive is an energetic plasticizer selected from the group of nitramines, such as butyl-NENA, dinitrodiazaalkane (DNDA), or is an explosive comprising RDX, HMX, FOX-7, FOX-12, and/or CL20.

6. The propellant composition according to claim 1, wherein the stabiliser consists of a component selected from a group consisting of alpha-tocopherol, beta-tocopherol, gamma-tocopherol, delta-tocopherol, alpha-tocotrienol, beta-tocotrienol, gamma-tocotrienol, delta-tocotrienol and a mixture thereof.

7. The propellant composition according to claim 1, wherein the stabiliser consists of a component selected from a group consisting of (+)-alpha-tocopherol, (+)-beta-tocopherol, (+)-gamma-tocopherol, (+)-delta-tocopherol, (−)-alpha-tocopherol, (−)-beta-tocopherol, (−)-gamma-tocopherol, (−)-delta-tocopherol and a mixture thereof.

8. The propellant composition according to claim 7, wherein said stabiliser consists of a mixture comprising (+)-alpha-tocopherol.

9. The propellant composition according to claim 1, wherein the stabiliser is present in the composition in an amount comprised between 0.1 and 5.0 wt. %, with respect to the total weight of the composition.

10. The propellant composition according to claim 1, wherein the nitrate ester-based propellant comprises not more than 60 wt. % nitroglycerine, with respect of the total weight of nitrate ester based propellant.

11. The propellant composition according to claim 1, having a stability measured according to STANAG 4582 (Ed. 1) at a temperature of 90° C. without heat generation above 350 µW/g of at least 3.43 days.

12. The propellant composition according to claim 1, further comprising one or more of the following compounds as complementary stabilisers:

(a) a substituted phenol compound having the general formula (13-I):

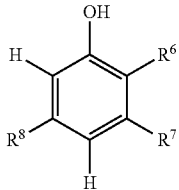
(13-I)

wherein: $R^6$ represents: (i) H, (ii) alkyl substituted or not, or (iii) an alkoxy group; and $R^7$ and $R^8$ are same or different, and represent (i) alkyl substituted or not, or (ii) alkoxy group;

(b) a trialkoxy benzene having the general formulae (14-1) or (14-II):

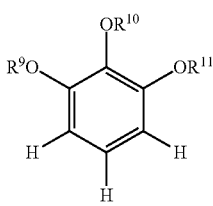
(14-I)

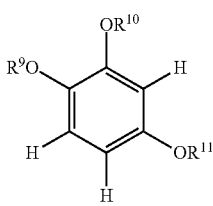
(14-II)

wherein $R^9$, $R^{10}$ and $R^{11}$ are same or different and represent $C_{1-5}$ alkyl unsubstituted or substituted with an alkoxy group;

(c) an aromatic compound having a general formula (15-I):

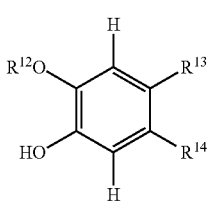
(15-I)

wherein: $R^{12}$ represents, alkyl substituted or not; $R^{13}$ represent (i) H, (ii) unsaturated alkyl group,
(iii)

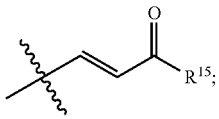

(iv)

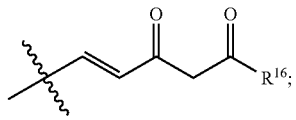

or (v)

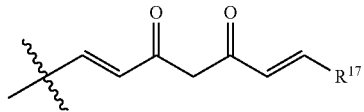

$R^{14}$ represents, H, alkyl substituted or not, or $OR^{18}$;

$R^{15}$ represents, alkyl substituted or not, aromatic ring substituted or not, or $OR^{18}$;

$R^{16}$ represents, alkyl substituted or not, aromatic ring substituted or not, or $OR^{19}$;

$R^{17}$ represents, aromatic ring substituted or not;

$R^{18}$ represents, alkyl substituted or not, or aromatic ring substituted; and $R^{19}$ represents, alkyl substituted or not, or aromatic ring substituted; and (d) a substituted phenol compound having the general formula (16-I):

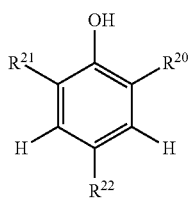
(16-I)

wherein: $R^{20}$, $R^{21}$ and $R^{22}$ are the same or different and represent: (i) alkyl-substituted or not, (ii) alkoxy group;

(e) a substituted phenol compound having the general formula (17-I):

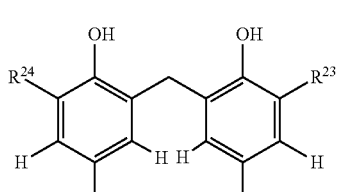
(17-I)

wherein: $R^{23}$, $R^{24}$, $R^{25}$ and $R^{26}$ are the same or different and represent: (i) alkyl-substituted or not, (ii) alkoxy group; and (f) a compound of the ionone-type, with a general formula (18-I), (18-II), (18-III) or (18-IV):

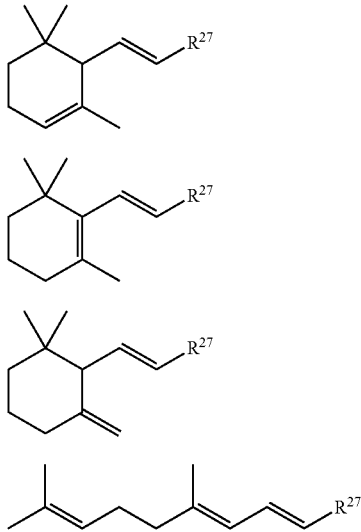

wherein $R^{27}$ represents a ketone, hydroxyl, carboxyl, aldehyde or unsaturated alkyl group.

13. The propellant composition according to claim 1, further comprising one or more of the following additives:
   (a) a potassium salt, such as potassium nitrate ($KNO_3$), in an amount comprised between 0.001 and 1.5 wt. %;
   (b) combustion moderators such as phthalates, Cl and citrate derivatives, in an amount comprised between 1.0 and 10.0 wt. %;
   (c) an anti-static agent such as graphite, in an amount comprised between 0.01 and 0.5 wt. %; and
   (d) calcium carbonate, in an amount comprised between 0.01 and 0.7 wt. %, wherein the wt. % are expressed in terms of the total weight of the propellant composition.

14. A method comprising:
   stabilising a nitrate ester based propellant comprising nitrocellulose with a component of a general formula (I):

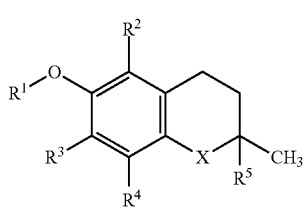

wherein:

X is oxygen;

$R^1$ is selected from the group consisting of hydrogen, alkyl, alkenyl, alkynyl, aryl, heteroaryl, carboxylic acid, carboxylate, ester, saccharide, alkoxy-linked saccharide, alcohol, and ethers;

$R^2$ is selected from the group consisting of hydrogen methyl, benzyl carboxylic acid, benzyl carboxylate, benzylester and saccharide;

$R^3$ is selected from the group consisting of hydrogen, methyl, benzyl carboxylic acid, benzyl carboxylate, benzylester and saccharide;

$R^4$ is selected from the group consisting of methyl, benzyl carboxylic acid, benzyl carboxylate, benzylester and saccharide; and $R^5$ is selected from the group consisting of alkyl and alkenyl.

15. The method according to claim 13, wherein the component of general formula (I) is selected
   from a group consisting of:
   (a) alpha-tocopherol, beta-tocopherol, gamma-tocopherol, delta-tocopherol, alpha-tocotrienol, beta-tocotrienol, gamma-tocotrienol, delta-tocotrienol and a mixture thereof,
   or from a group consisting of:
   (b) (+)-alpha-tocopherol, (+)-beta-tocopherol, (+)-gamma-tocopherol, (+)-delta-tocopherol, (−)-alpha-tocopherol, (−)-beta-tocopherol, (−)-gamma-tocopherol, (−)-delta-tocopherol and a mixture thereof.

16. The propellant composition according to claim 9, wherein the stabiliser is present in the composition in an amount comprised between 0.2 and 2.0 wt. %, with respect to the total weight of the composition.

17. The propellant composition according to claim 16, wherein the stabiliser is present in the composition in an amount comprised between 0.5 and 1.0 wt. %, with respect to the total weight of the composition.

18. The propellant composition according to claim 10, wherein the nitrate ester-based propellant comprises between 5 and 45 wt. % nitroglycerine, with respect of the total weight of nitrate ester based propellant.

19. The propellant composition according to claim 18, wherein the nitrate ester-based propellant comprises between 7 and 22 wt. % nitroglycerine, with respect of the total weight of nitrate ester based propellant.

20. The propellant composition according to claim 11, having a stability measured according to STANAG 4582 (Ed. 1) at a temperature of 90 without heat generation above 350 µW/g of at least 10 days.

* * * * *